(12) United States Patent
Adams et al.

(10) Patent No.: US 11,403,722 B2
(45) Date of Patent: Aug. 2, 2022

(54) COMPLIANCE SYSTEM FOR REDUCING FRAUD IN THE PROVISION OF NON-EMERGENCY MEDICAL TRANSPORTATION SERVICES

(75) Inventors: Steve Adams, Atlanta, GA (US); James Degliumberto, Atlanta, GA (US)

(73) Assignee: Southeastrans, Inc., Atlanta, GA (US)

( * ) Notice: Subject to any disclaimer, the term of this patent is extended or adjusted under 35 U.S.C. 154(b) by 0 days.

(21) Appl. No.: 13/349,825

(22) Filed: Jan. 13, 2012

(65) Prior Publication Data

US 2013/0185221 A1 Jul. 18, 2013

(51) Int. Cl.
*G06Q 50/28* (2012.01)
*G06Q 50/30* (2012.01)
*G16H 40/20* (2018.01)

(52) U.S. Cl.
CPC ............ *G06Q 50/28* (2013.01); *G06Q 50/30* (2013.01); *G16H 40/20* (2018.01)

(58) Field of Classification Search
CPC .. G06Q 10/02; G06Q 10/083; G06Q 10/0832; G06Q 10/0833; G06Q 10/0835; G06Q 10/0837; G06Q 50/28
USPC ........................................................ 705/333
See application file for complete search history.

(56) References Cited

U.S. PATENT DOCUMENTS

| | | | | |
|---|---|---|---|---|
| 6,042,383 A | * | 3/2000 | Herron | 434/238 |
| 2001/0047286 A1 | * | 11/2001 | Walker | H04L 67/18 705/7.13 |
| 2002/0095326 A1 | * | 7/2002 | Katz | 705/9 |
| 2002/0183920 A1 | * | 12/2002 | Smith et al. | 701/117 |
| 2003/0097428 A1 | * | 5/2003 | Afkhami et al. | 709/220 |
| 2004/0128134 A1 | * | 7/2004 | Sacks et al. | 704/270 |
| 2005/0131740 A1 | * | 6/2005 | Massenzio et al. | 705/2 |
| 2005/0197848 A1 | * | 9/2005 | Chou et al. | 705/1 |
| 2006/0004604 A1 | * | 1/2006 | White | 705/2 |
| 2006/0238334 A1 | * | 10/2006 | Mangan | G06Q 10/0833 340/539.13 |
| 2006/0286965 A1 | * | 12/2006 | Lauridsen et al. | 455/410 |
| 2007/0034107 A1 | * | 2/2007 | Barbeau et al. | 104/307 |

(Continued)

OTHER PUBLICATIONS

Cabconnect, "Featured Solution" (retrieved Oct. 15, 2010, available at: https://web.archive.org/web/20101015031537/http://cabconnect.com/solutions.html).*

(Continued)

*Primary Examiner* — Emmett K. Walsh
(74) *Attorney, Agent, or Firm* — Renner, Otto, Boisselle & Sklar, LLP

(57) ABSTRACT

A system for rendering delivery services is provided which includes a portable data collection device. The portable data collection device includes an integrated location determination system. A trip schedule for an individual or item including a pickup location and a drop off location is provided to the portable data collection device. A respective location identifier is associated with the pickup and drop off locations. The location determination system of the portable data collection device provides a location of the portable data collection device at the occurrence of a pickup or dropoff. The location identifiers associated with the pickup and drop off locations are compared with the location of the portable data collection device at the pickup and drop off locations.

4 Claims, 16 Drawing Sheets

(56) References Cited

U.S. PATENT DOCUMENTS

| | | | |
|---|---|---|---|
| 2007/0096900 A1* | 5/2007 | Contractor | 340/539.13 |
| 2008/0058615 A1* | 3/2008 | Clapp et al. | 600/301 |
| 2009/0228300 A1* | 9/2009 | Hamel | G06Q 30/0185 |
| | | | 705/2 |
| 2010/0198608 A1* | 8/2010 | Kaboff et al. | 705/2 |
| 2011/0060600 A1* | 3/2011 | Fox et al. | 705/1.1 |
| 2011/0112761 A1* | 5/2011 | Hurley | G01C 21/32 |
| | | | 701/465 |
| 2012/0130627 A1* | 5/2012 | Islam | G08G 1/202 |
| | | | 701/300 |
| 2013/0024387 A1* | 1/2013 | Dillon | G06Q 10/0833 |
| | | | 705/317 |
| 2013/0090939 A1* | 4/2013 | Robinson et al. | 705/2 |

OTHER PUBLICATIONS

"New York State Medicaid Program: Transportation Manual Policy Guidelines," Oct. 20, 2006, available at: https://www.emedny.org/ProviderManuals/Transportation/PDFS/Archive/Transportation_Manual_Policy_Section2006-1.pdf.*

Arndt, Jeffrey C., and Linda Kay Cherrington. The Role of Private-for-Hire Vehicles in Transit in Texas. No. FHWA/TX-08/0-5545-1. Texas Transportation Institute, Texas A & M University System. (Year: 2007).*

* cited by examiner

| MEMBER | PICKUP LOCATION | PICK UP TIME | FACILITY LOCATION | DROP OFF TIME | FACILITY PICK UP LOCATION | MEMBER DROP OFF LOCATION | MEMBER DROP OFF TIME |
|---|---|---|---|---|---|---|---|
| Jane Smith | 123 Elm Street, New York, New York | 12:30 PM | 111 A Street, New York, New York | 1:15 P.M. | 111 A Street New York, New York | 123 Elm Street, New York, New York | 5:00 PM |
| Elvin Jones | 193 Elm Street, New York, New York | 12:45 P.M. | 135 B Street, New York, New York | 1:27 | 135 B Street, New York, New York | 193 Elm Street, New York, New York | 5:15 PM |
| Sally Brown | 622 Chester Street, New York, New York | 1:45 | 201 C Street, New York, New York | 2:00 | 201 C Street, New York, New York | 622 Chester Street New York, New York | 5:30 |

FIG. 8

Driver Name *: [JimDegliumberto]

If this is not you please cancel this record and log this driver out using the "Settings" button from the "Action Menu". Then log in with your ID.

Daily Vehicle Inspection Complete *

| Yes | No |

License Plate # *

Complete Vehicle Mileage *

VIN Number (Last 4) *

SET Inspection Decal Number *

Attendant/Monitor's Name

Driver Signature *

DONE

COMPLIANCE SYSTEM FOR REDUCING FRAUD IN THE PROVISION OF NON-EMERGENCY MEDICAL TRANSPORTATION SERVICES

FIELD OF INVENTION

The present invention relates to monitoring the provision of nonemergency medical transportation services and more particularly to the utilization of geocodes associated with the location of respective members and their respective appointments for determining compliance of the provision of services with the respective requested services.

BACKGROUND OF INVENTION

Pursuant to Title XIX of the Social Security Act, the Medicaid program provides medical assistance to low-income individuals and individuals with disabilities. Federal and State Governments jointly fund the Medicaid Program. Each State administers its Medicaid program in accordance with Federal guidelines set forth by the Centers for Medicare & Medicaid Services. Pursuant to 42 CFR § 440.170, the transportation benefit includes transportation expenses and related travel expenses deemed necessary by the State Medicaid agency to secure medical examinations and treatment for a Medicaid beneficiary.

The Deficit Reduction Act of 2005 gave States the option to establish a non-emergency medical transportation brokerage program in order to cost-effectively provide transportation for Medicaid beneficiaries. In addition to the utilization of brokerage services, Federal regulations require that each State Medicaid agency establish a program integrity program that includes methods for identifying and investigating suspected fraud and abuse cases. Many of these programs focus on screening the transportation providers, requiring prior approval of services and implementing methods to prevent and detect improper billing. In a recent study conducted by the Department of Health & Human Services, Office of Inspector General dated May 28, 2009, entitled "Memorandum Report: Fraud and Abuse Safeguards for State Medicaid Nonemergency Medical Transportation Services" it was noted all fifty states reported implementing one or more methods to prevent and detect improper billing. Such systems included operating public hotlines, analysis of claims data for irregular billing, and other data mining techniques.

Twenty-nine states utilized brokers to administer all or part of the NEMT programs. Other states utilized brokers in some capacity for administration of the NEMT programs. In most of these situations, the brokers were required to administer the processes necessary to insure program compliance. Additionally, some states paid the brokers on a capitated payment schedule which shifted the risk of improper NEMT payments from the state to the broker.

In the cited study, a larger number of fraud and abuse cases were cited. The two most common types involved provider billing fraud, including billing for services not rendered and unspecified overbilling. Other common types included billing for excess mileage and for nonmedical use of NEMT services.

Accordingly, with the occurrence of fraud in the NEMT industry, there is a need for a system which will reduce the ability of fraud to occur. Also, there is a need for brokers to have a system for monitoring the compliance of the services of the service providers for the reduction of fraud.

It is an object of the present invention to provide for a system which may provide sufficient information to reduce the occurrence of fraud in the provision of NEMT services.

SUMMARY OF THE INVENTION

The above objectives are accomplished according to the present invention by providing a system for rendering delivery services which includes a portable data collection device. The portable data collection device includes an integrated location determination system and also includes a processor, an input device, and a wireless communication system. A trip schedule for an individual or item including a pickup location and a drop off location is provided to the portable data collection device. A respective location identifier is associated with the pickup and drop off locations. The trip schedule is displayed to an individual via the portable data collection device. The occurrence of a pickup is noted utilizing the portable data collection device. The location determination system of the portable data collection device provides a location of the portable data collection device at the occurrence of the pickup. The occurrence of a drop off is noted utilizing the portable data collection device. The location determination system of the portable data collection device provides a location identifier of the portable data collection device at the occurrence of the drop off. The location identifiers associated with the pickup and drop off locations are compared with the location of the portable data collection device at the pickup and drop off locations.

DESCRIPTION OF DRAWINGS

The construction and design to carry out the invention will hereinafter be described together with other features thereof. The invention will be more readily understood from a reading of the following specification and by reference to the accompanying drawings forming a part thereof, wherein an example of the invention is shown and wherein:

FIG. 4 illustrates a data entry form to create member data for a respective member according to the preferred embodiment of the present invention.

FIG. 5 illustrates a data entry form to create facility data for a respective facility according to the preferred embodiment of the present invention.

FIG. 6 illustrates a provider record of a respective service provider according to the preferred embodiment of the present invention.

FIG. 7 illustrates a data entry from for the entry of a scheduled trip for a respective member according to the preferred embodiment of the present invention.

FIG. 8 illustrates a manifest and respective itineraries for a transportation provider for display on a data collection device according to the preferred embodiment of the present invention.

FIG. 10 illustrates a driver sign in screen displayed by the portable data collection device according to the preferred embodiment of the present invention.

FIG. 11 illustrates a pickup data entry screen displayed by the portable data collection device according to the preferred embodiment of the present invention.

DETAILED DESCRIPTION OF PREFERRED EMBODIMENTS

Figure 1A:
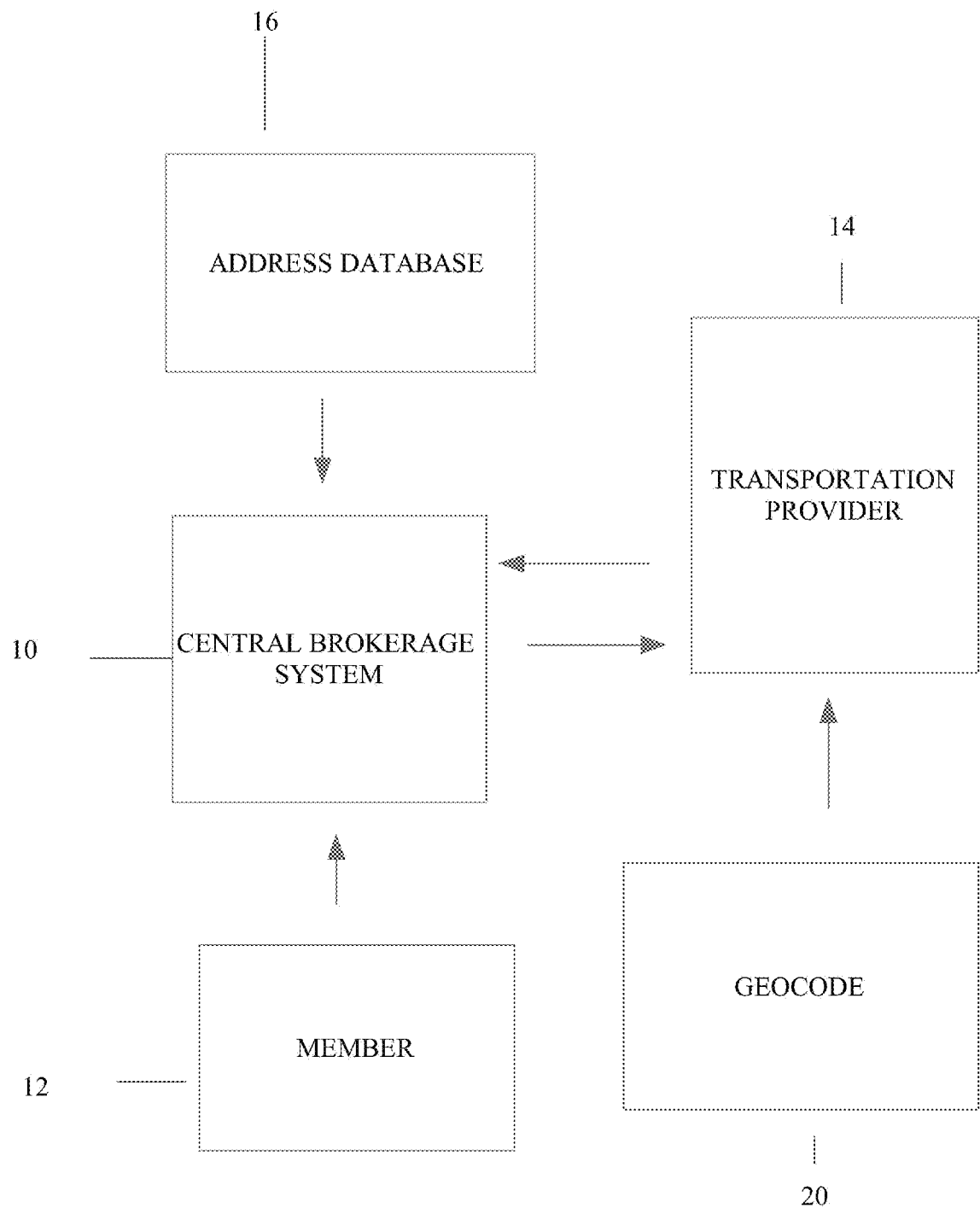
FIG. 1A illustrates the interrelationship of the members and transportation providers with a central brokerage system according to the preferred embodiment of the present invention.

Referring now to the drawings, the invention will now be described in more detail. In the following description, referring to the drawings in general, the illustrations are for the purpose of describing a preferred embodiment of the invention and are not intended to limit the invention thereto.

The system provides a mechanism for detecting fraudulent activity and notifying those of that activity. The system has the capability to alert those affected based on a number of predetermined indicators. This system is designed to assist those who need to validate the occurrence of an event such as the transport of an item. Those needed to validate such items include medical providers, transportation agencies, transportation companies, insurance agencies, managed care organizations, etc.

Figure 15:
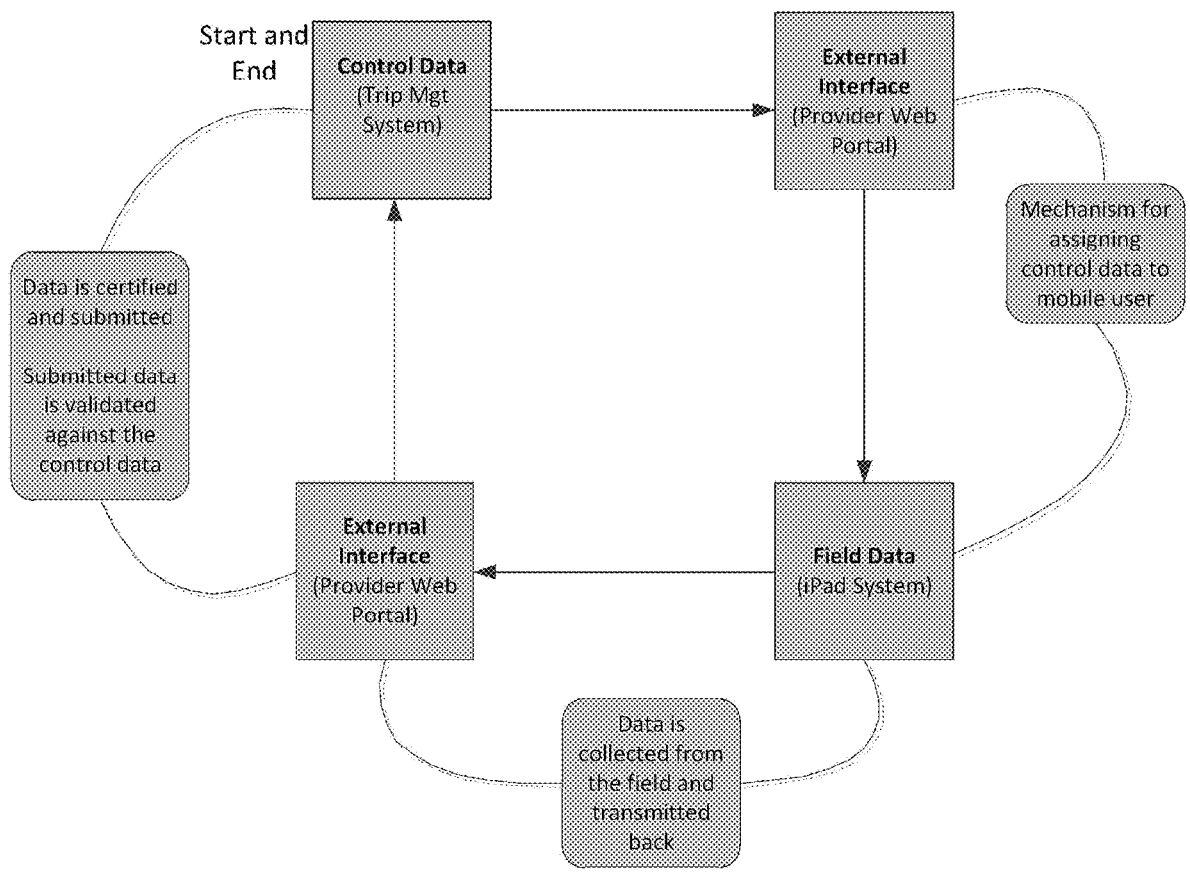
FIG. 15 illustrates the interrelationship of the components of the system including the trip management system, web portal, and data collection device according to the preferred embodiment of the present invention.

As shown in FIG. 15, the system consists of a control system, an external interface of $3^{rd}$ party verification and a mobile data collection device. The control system receives and stores information about the item. This information includes the items identifying data (name, ID numbers), its characteristics (age, size, type) and the information regarding its transportation such as carrier, date, time, location (GPS coordinates). The information contained within the control system is stored in a relational database.

The external interface for $3^{rd}$ party verification serves as a communication mechanism with $3^{rd}$ parties who do not have access to the control system. To ensure data integrity within the control system this external interface serves as the intermediary communicating entity with the control system and the mobile data collection device. This external interface uses web technologies such as the Microsoft.net framework and stores its data within a relational database.

The mobile data collection device receives its core information from the external interface. Information viewed within the external interface is assigned to the mobile data collection device and through cellular and WiFi networks this information is transmitted between the two systems. In addition to the information provided to the mobile data collection device the mobile data collection device captures event data from the field. This data includes time stamped event activities, GPS location information, transportation method information (which vehicle is it in), receipt confirmation data in the form of an electronic signature, voice print, image, RFID reading or barcode scan.

As shown in FIG. 1A, the preferred embodiment relates to a non emergency medical transportation environment wherein respective medical patients, members, are transported to and from their respective medical appointments via a third party transportation provider. In the preferred embodiment, a central brokerage system 10 is utilized wherein the respective member 12 corresponds with the brokerage system identifying the need for transportation services and the brokerage system organizes the appropriate services with a particular transportation provider 14. In the preferred embodiment, address data 16 is utilized for identifying the respective addresses of the member requesting the transportation services and the associated appointment location. This address data serves two purposes. Initially it assists the brokerage service in identifying the appropriate transportation provider and it also associates geocode information with the requesting member and the associated appointment location. This geocode information may constitute the longitude, latitude, coordinate reference system, or other geospatial attribute of the locations. An itinerary is created for the transportation provider identifying the respective location of member pickup and drop off. The preferred embodiment utilizes the appropriate geocode information for cross-checking the performance of the transportation provider.

Preferably the geocode information 20 of the location where the transportation provider picks up the respective member is noted by a location determination system such as a gps system associated with the transportation provider as well as the geocode information for the location where the transportation provider drops the member off for the respective appointment. The geocodes of the actual locations of the member pickup and drop off are cross-checked with the respective geocodes of the initial member itinerary. Should a discrepancy exist between the respective geocodes the remittance of funds for the services provided by the transportation provider may be denied.

Figure 1B:
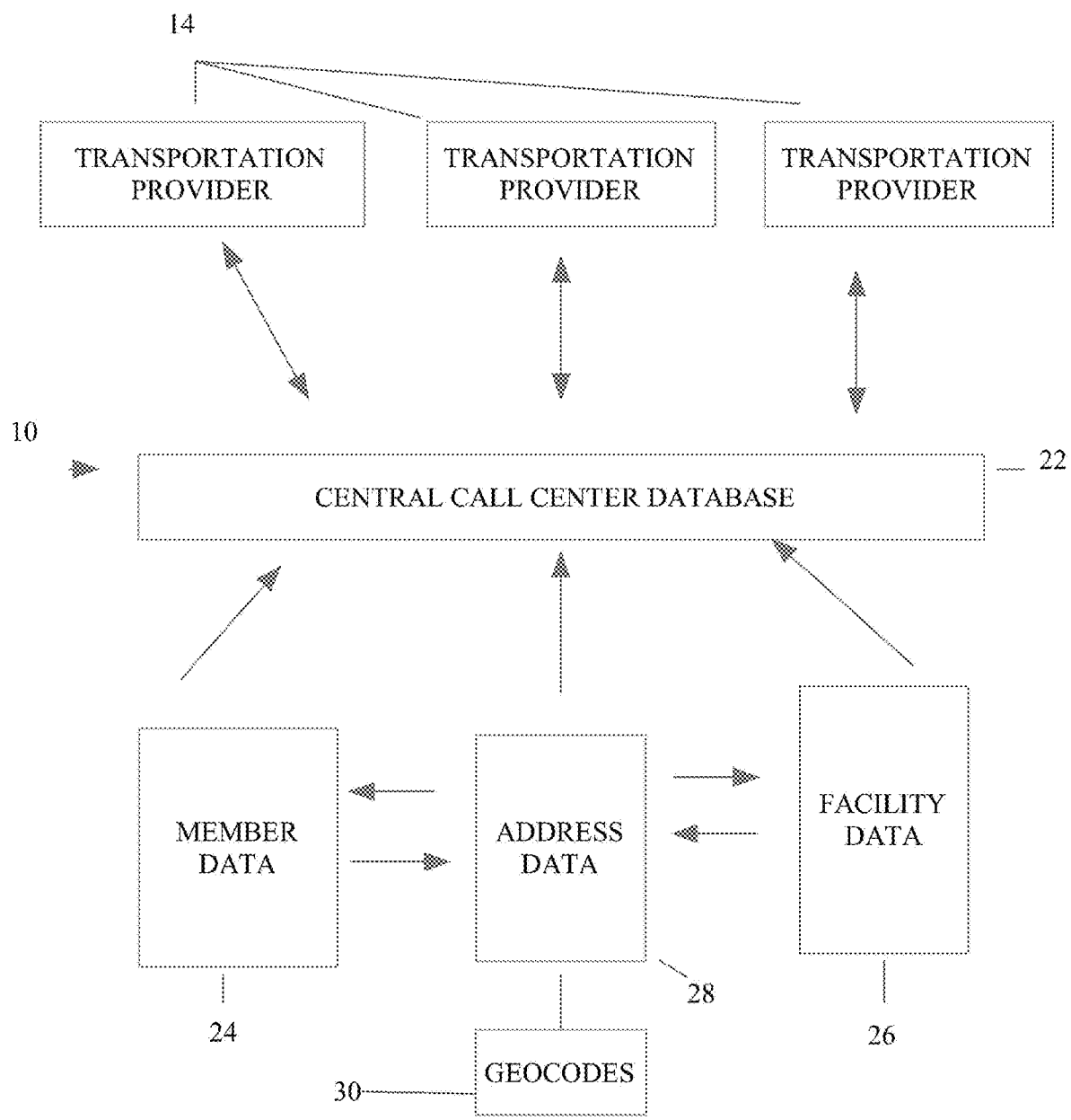
FIG. 1B illustrates the interrelationship of the members, transportation providers, and facility data with a central call center database utilized by a central brokerage system according to the preferred embodiment of the present invention.

Central brokerage system 10 facilitates the assignment of requested member medical visits with corresponding transportation providers. As shown in FIG. 1B, central brokerage system 10 utilizes a central call center database 22. Central call center database 22 includes member data records 24 which corresponds to the respective members who will utilize the central brokerage system for scheduling the pick and delivery services of a transportation provider for attending appointments at a facility location, facility data records 26 corresponding to the facility location where services will be provided, address data records 28 which corresponds to addresses of the members and facilities, geocodes database 30 which correspond with the respective addresses identified by address data 28.

Figure 2:
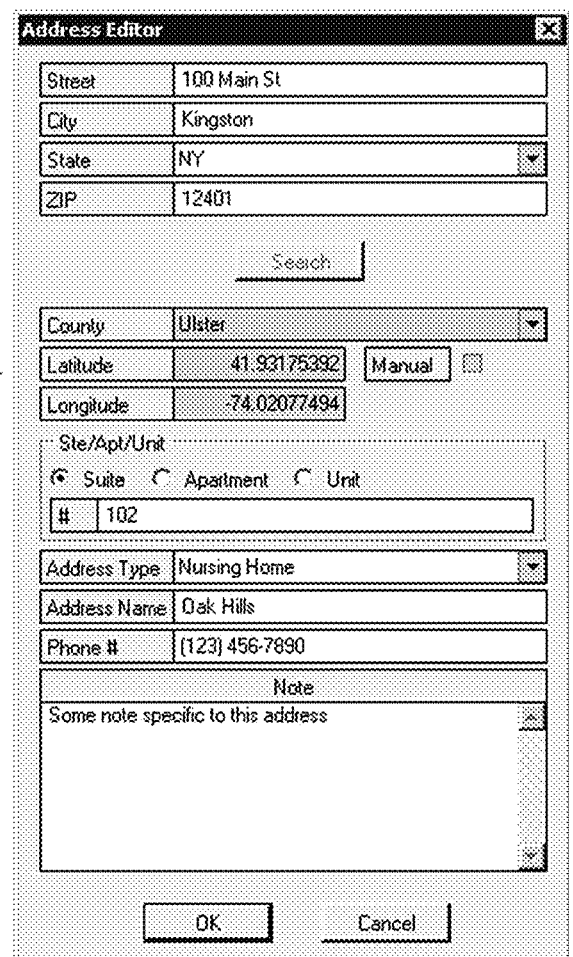
FIG. 2 illustrates a data entry form to create address data for a respective member or facility according to the preferred embodiment of the present invention.
Figure 3:
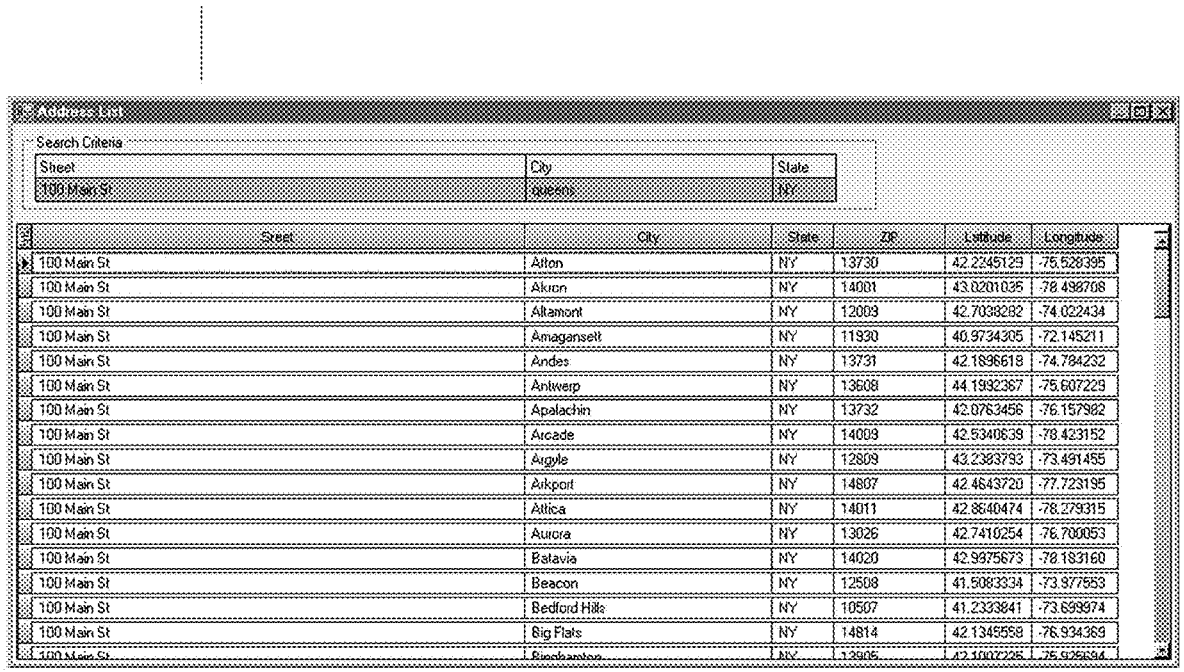
FIG. 3 illustrates geocodes associated with an address for utilization by the preferred embodiment of the present invention.

FIG. 2 illustrates a typical data entry form to create address data 28 for a respective member or facility. As noted in FIG. 2 in addition to the general address information such as street, city, zip code, the address data includes the type of address, such as either residential, hospital, nursing home, which would correspond to a member of a facility. Also, geocodes 32 are derived from a geocode database 30 and associated with the respective address. FIG. 3 identifies a geocode database 30 which includes respective geocode information which corresponds with the appropriate address.

This geocode information will be utilized as a control reference data for validating the accuracy of the transportation provider's services.

Figure 4:
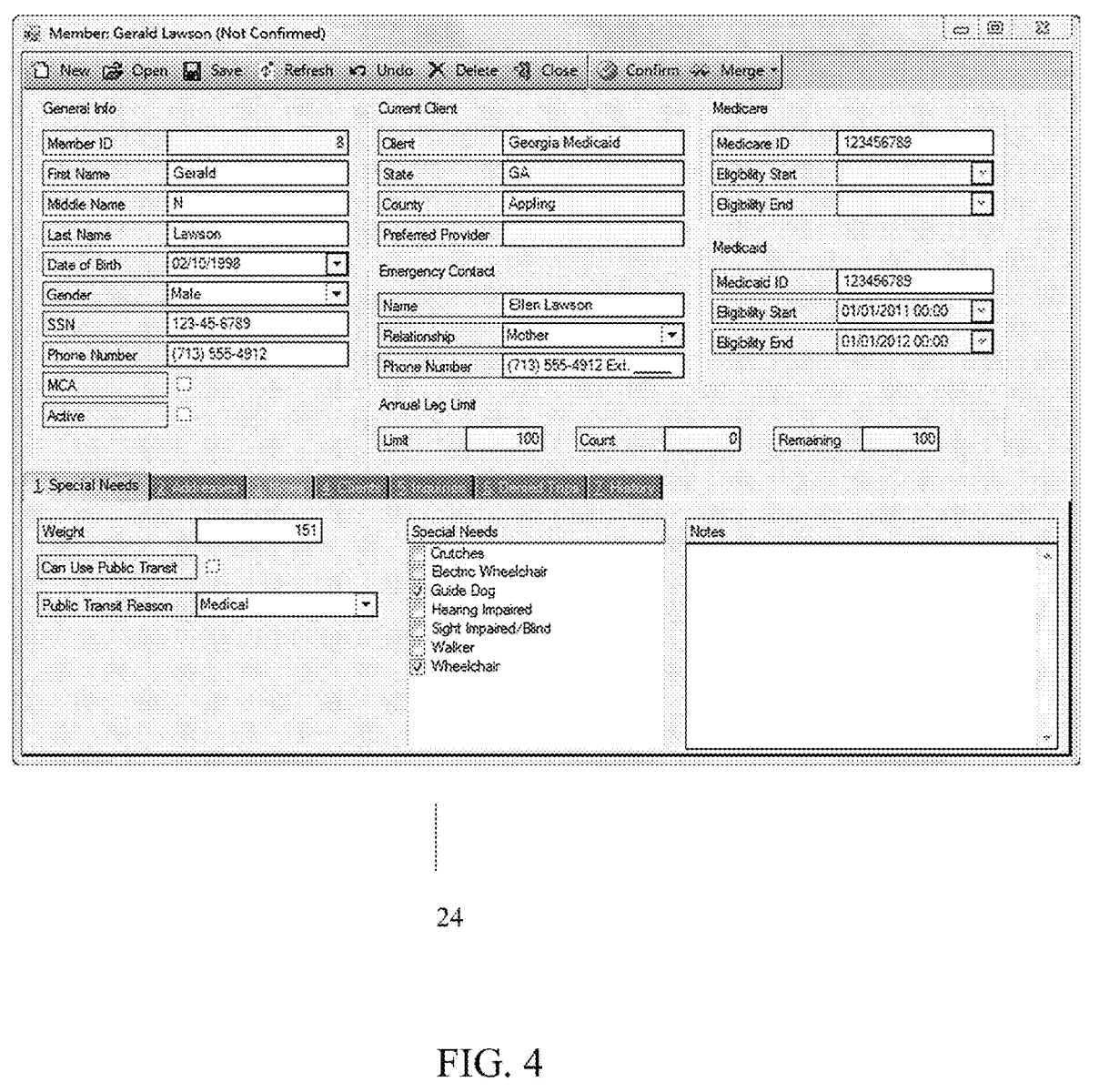

FIG. 4 illustrates a typical data entry form for establishing the creation of a member data record 24. The member data record includes the member's name, address, which client they are associated with such as Medicaid, and special needs such as a wheelchair or a guide dog. A unique member record will be established for each member who utilizes the broker's services in fulfilling requests for transportation services. An address data record will be associated with the respective member record. Additional data entry fields will include history of trips, and certain member verification data such as social security number, a Medicare ID, or a signature block, a voice signature file, or some other individual related record which will be utilized to authenticate the provision of services by the member.

Figure 5:
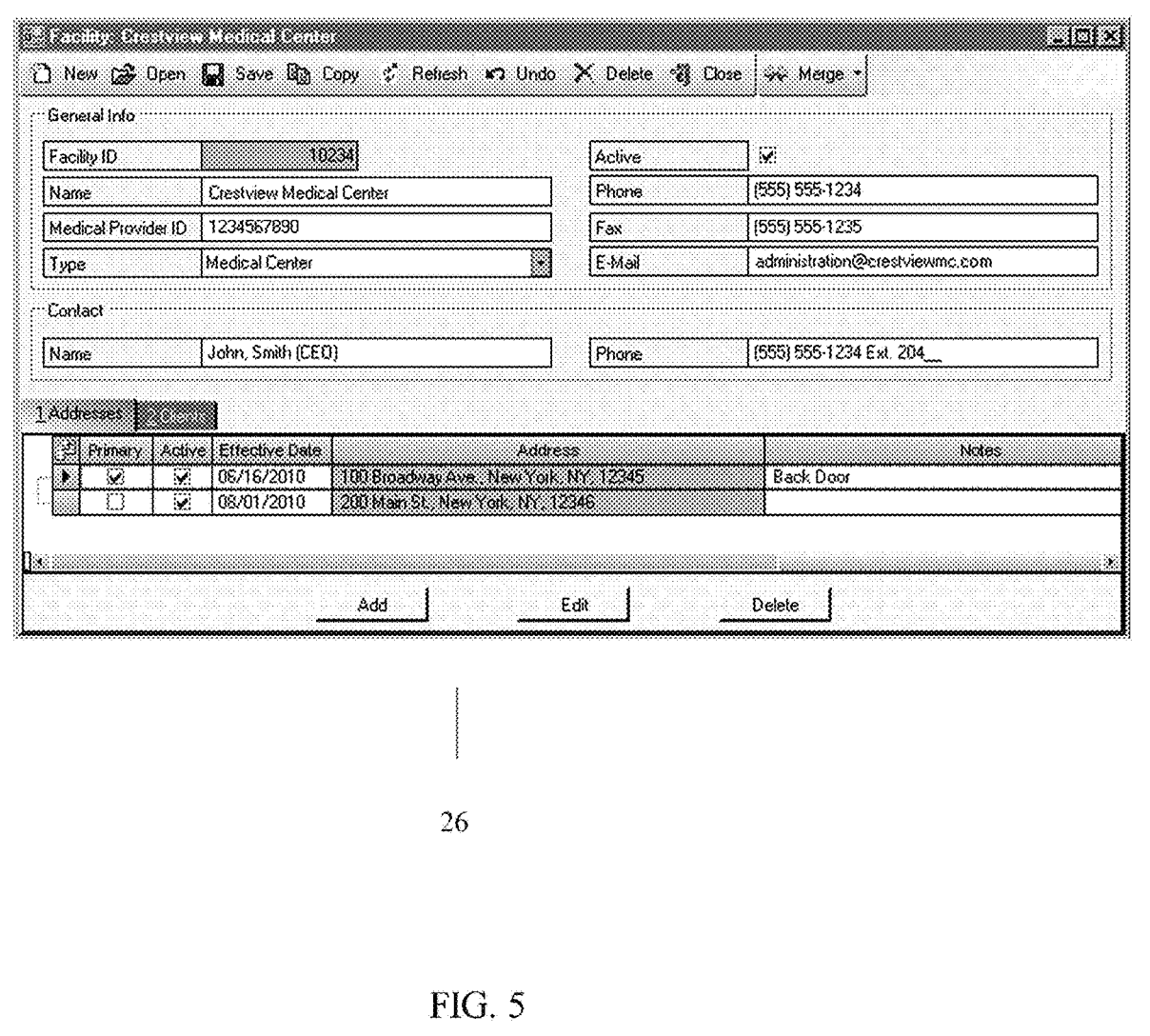

FIG. 5 illustrates a representative facility data record. Facility data record 26 includes information relating to the location of the facility where an appointment is scheduled. This record includes the address of the location which will have a corresponding geocode associated with it. This data record also preferably includes the facility type, a contact name and the name of the location.

Figure 6:
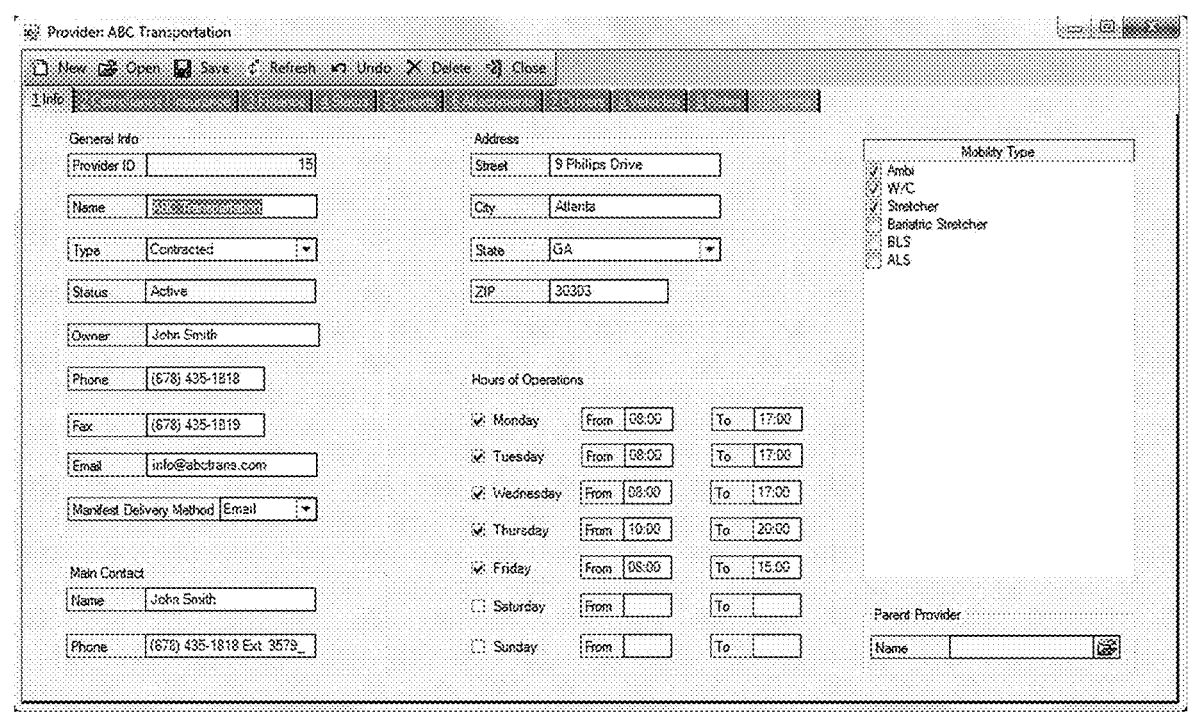

FIG. 6 illustrates a provider data record. A provider is an establishment which provides transportation services to the members. As shown in FIG. 6, the provider record includes multiple components. These distinct components include general information such as the name of the provider, contact information and address. Additionally, the provider is identified with specific drivers, vehicles and rates. The rates may be based on mileage, hourly, no shows in addition to ancillary rates.

Figure 7:
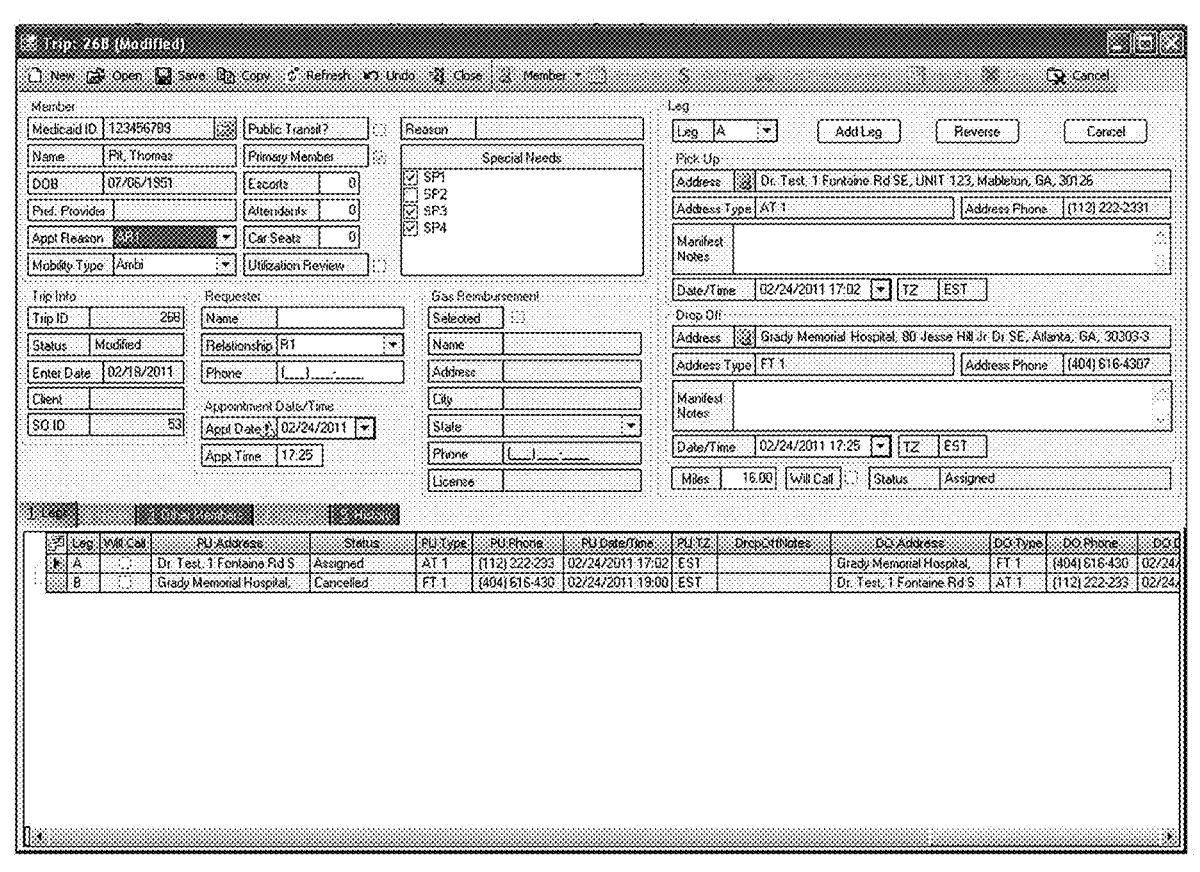

FIG. 7 illustrates a data entry screen for the entry of a scheduled trip. In the preferred embodiment of the present invention, a member who requires transportation will call a centralized broker or dispatcher who will input the requirements of the particular member for attending a predetermined appointment with a previously identified facility. As shown in FIG. 7, a typical data record would include the member's name, a pickup location which would have an associated geocode and an associated date and time, a drop off location for the appointment which would have an associated geocode and an associated date and time, and a composite itinerary if multiple trip legs are required for this particular visit such as an initial visit to a doctor facility and a subsequent visit to a lab for certain procedures. The additional visits would have their own individual trip leg record, however a single itinerary of all trips would be provided. Also, the trip record includes the members name and an additional member identification item such as the members Medicaid ID number.

The trips are entered into a trips database. A dispatching system is utilized for coordinating the assemblage of trips for subsequent dispatching to various service providers. The trips may be dispatched to various service providers as a single trip involving a single member, or a group trip comprised from multiple members from a single facility such as a nursing home or other health care center. The trips may be dispatched to a single service provider based on the proximity of the provider to the services requiring rendering, or the trips may be submitted to various providers for bidding if multiple providers are located within a desired area and the multiple providers are all capable of fulfilling the requirements of providing the services. The respective trip will include a trip id number. Multiple members may be associated with a respective trip if the scheduled trip is a group trip.

Once the respective trips have been allocated to a specific provider, the provider preferably bundles the trips and the respective itineraries into a manifest for a certain vehicle and associated driver for providing the services. Prospective itineraries are shown in FIG. 8. These itineraries include multiple member routes which include the member names, their respective pickup locations and pickup time, their respective facility or appointment locations and respective appointment times. Additional information relating to a trip might also include the respective pickup location and a respective drop off time. Each of these locations will have a geocode associated with the respective pickup and drop off location.

Once a manifest of multiple trips for multiple individuals and trips is compiled, the manifest is assigned to a transportation provider, namely an authorized driver of an authorized vehicle. The authorized driver is responsible for ultimately providing the transportation services. The performance of the authorized driver will result in the transportation provider being reimbursed for the services rendered.

Figure 9:
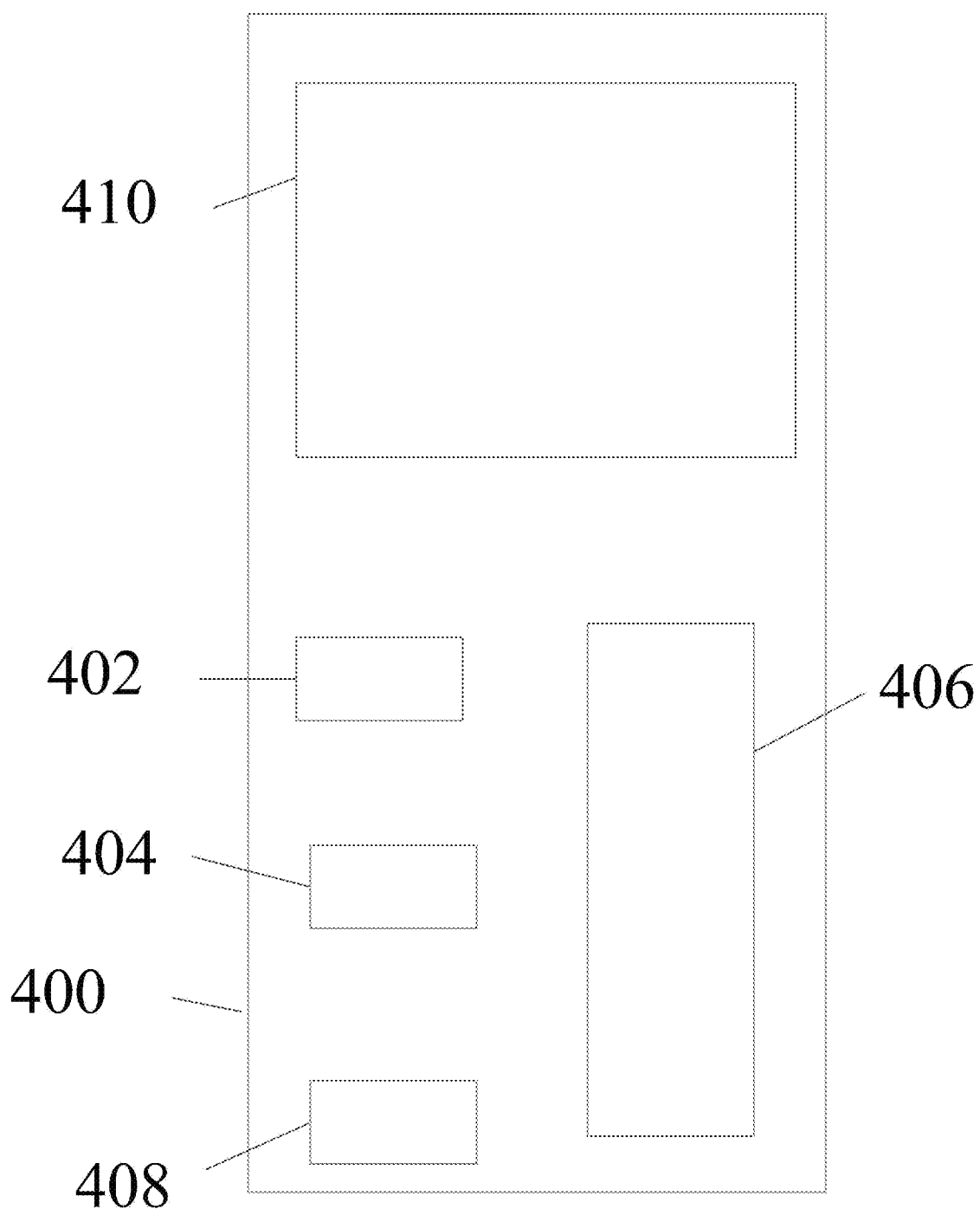
FIG. 9 illustrates a portable data collection device according to the preferred embodiment of the present invention.

As shown in FIG. 9, the authorized driver is provided with a data collection device 400. Data collection device 400 is preferably a computer which includes a processor 402, physical memory 404, a display 410 and a data input device 406. In the preferred embodiment data collection device 400 is a portable hand held device such as an Apple® Ipad® or Android® tablet which includes a location positioning device 408 for determining the physical location of the associated data collection device 400. The data collection device 400 also includes the ability to receive information such as the manifest and respective itineraries for a particular driver via a wireless connection or via an application which may be accessed through a secured and encrypted internet connection.

In operation, as shown in FIG. 10, to ensure the integrity of the system, the driver is required to input various identification features such as his name, vehicle registration number and the like. This information is utilized for establishing a transaction receipt which is ultimately utilized for reimbursing the driver for his services. Accordingly, the data collection device 400 is utilized for initializing the transaction record prior to the commencement of the rendering of the services. Once the initialization of the transaction record has been established, the driver is able to retrieve the particular manifest of trips associated with that driver. The driver's identification key is utilized for accessing the previously established manifest associated for that particular driver. One the driver initiates the transaction record the manifest and respective itineraries affiliated for the driver is downloaded to the respective data collection device 400. As previously noted, the manifest will include the identification of the particular members who require transportation services, their respective pickup and drop off times and locations and the times.

Preferably, the respective itineraries are displayed by the data collection device 400. When the driver initiates the first pickup as identified by the itineraries a compliance system is utilized for ensuring the integrity of the driver's performance in conducting the required pickup. The compliance system may include a couple of different features. Primarily, the security system utilizes a location determination device 408 affiliated with data collection device 400. Location determination device 408 may be any standard GPS type system which provides data associated with the location of a respective device. Accordingly, data collection device 400 utilizes a system which provides the location of the respective data collection device when such location is requested. The security system may also utilize a time stamp when a particular member is picked up and dropped off.

Figure 11:
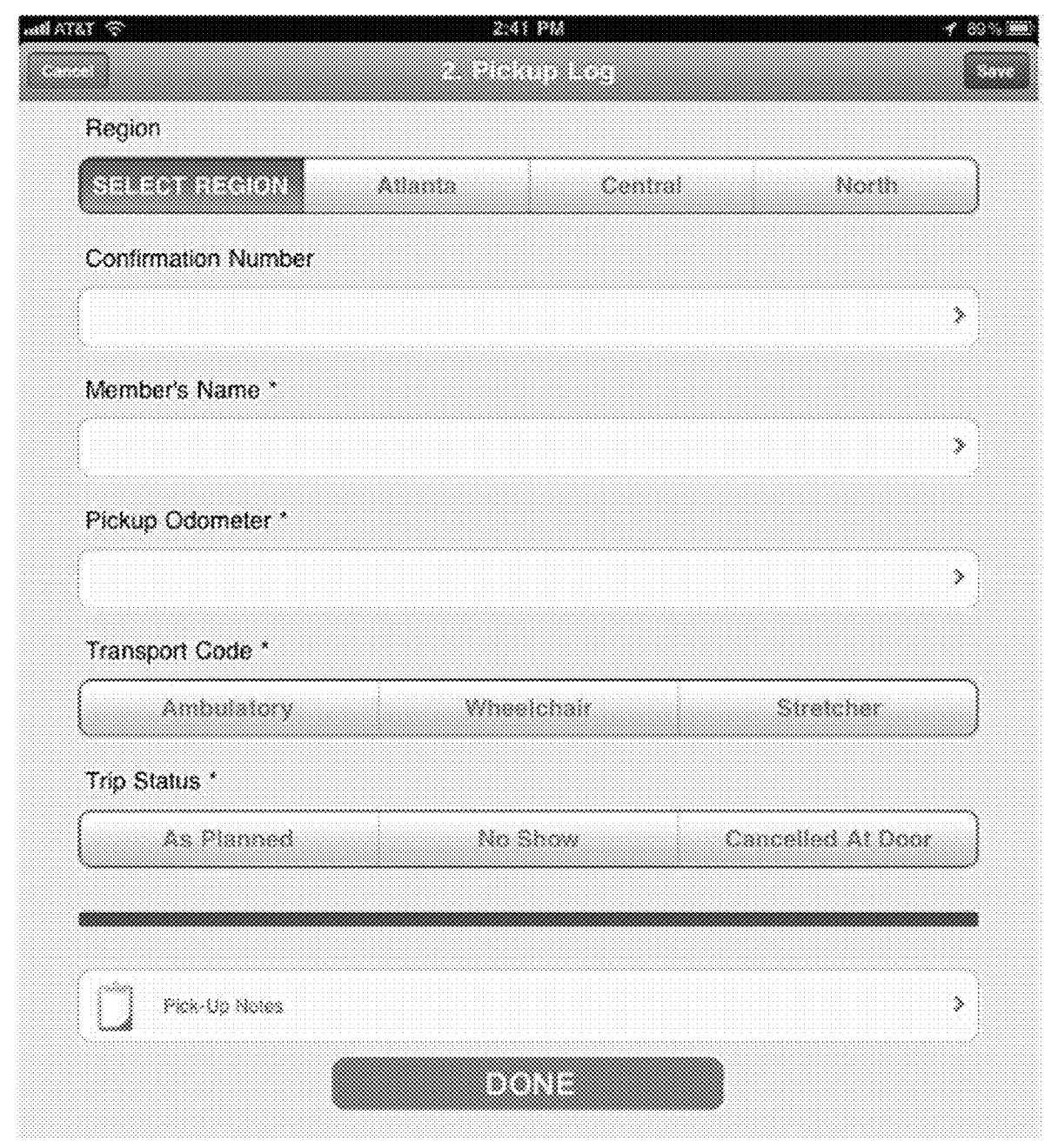

As shown in FIG. 11 when the driver makes the required pick as identified in the itinerary, a pickup acknowledgement is required. In the preferred embodiment, the reimbursement application which includes the initialization of a transaction record and trip itineraries also includes a procedure wherein an affirmative action is required with the application for acknowledging that the pickup occurred at the requested time and location. Preferably, the pickup acknowledgement includes the member who is picked up providing a unique member identifier. This unique member identifier may consist of the member's signature, social security number, a unique trip ID number assigned when the trip was originally scheduled, a voice recording, a finger print rendering, or some other unique identifier. The occurrence of the inputting of the unique member identifier triggers two distinct actions. First, the time of occurrence is noted, and second the location determination device 408 determines the location of the data collection device at the time of the inputting of the unique member identification and establishes a pickup location geocode for the pickup event. This pickup geocode will be compared to the geocode associated with the previously identified pickup location associated with the respective trip when the trip was originally established.

Figure 12:
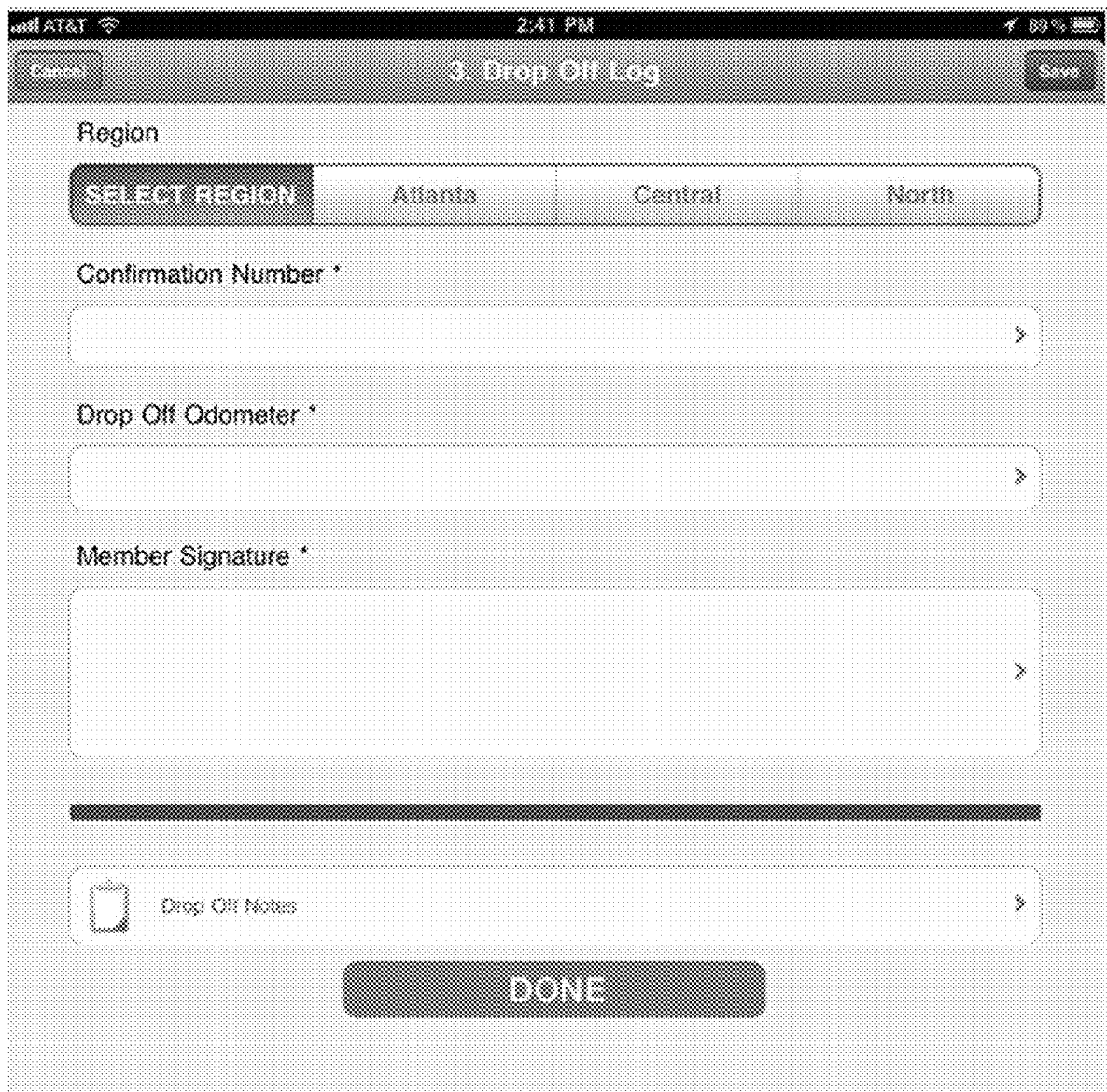
FIG. 12 illustrates a drop off data entry screen displayed by the portable data collection device according to the preferred embodiment of the present invention.

As shown in FIG. 12, in addition to the pickup acknowledgement record, a drop off acknowledgment record is also required. Like the pickup acknowledgement record, the drop off acknowledgment record is a unique identifier which is preferably similar to the unique member identifier utilized as the pickup acknowledgment record. For instance, when the member is dropped off at the required facility, the member is required to acknowledge that the drop off task has been completed. When the member provides the unique member identifier verifying the drop off, the time is noted and the respective geocode of the drop off location is provided by the location determination device as a drop off geocode. The drop off geocode will be compared to the geocode associated with the previously identified drop off location associated with the respective trip when the trip was originally established.

Thus, the system includes separate checks to ensure that the trip as scheduled actually occurred. The geocodes affiliated with the respective pickup and drop off locations are compared with the actual geocodes affiliated with the specific location of the data collection device when the actual pickup and drop off events occurred and the time is noted and compared to the originally scheduled times for pickups and drop offs.

Figure 14:
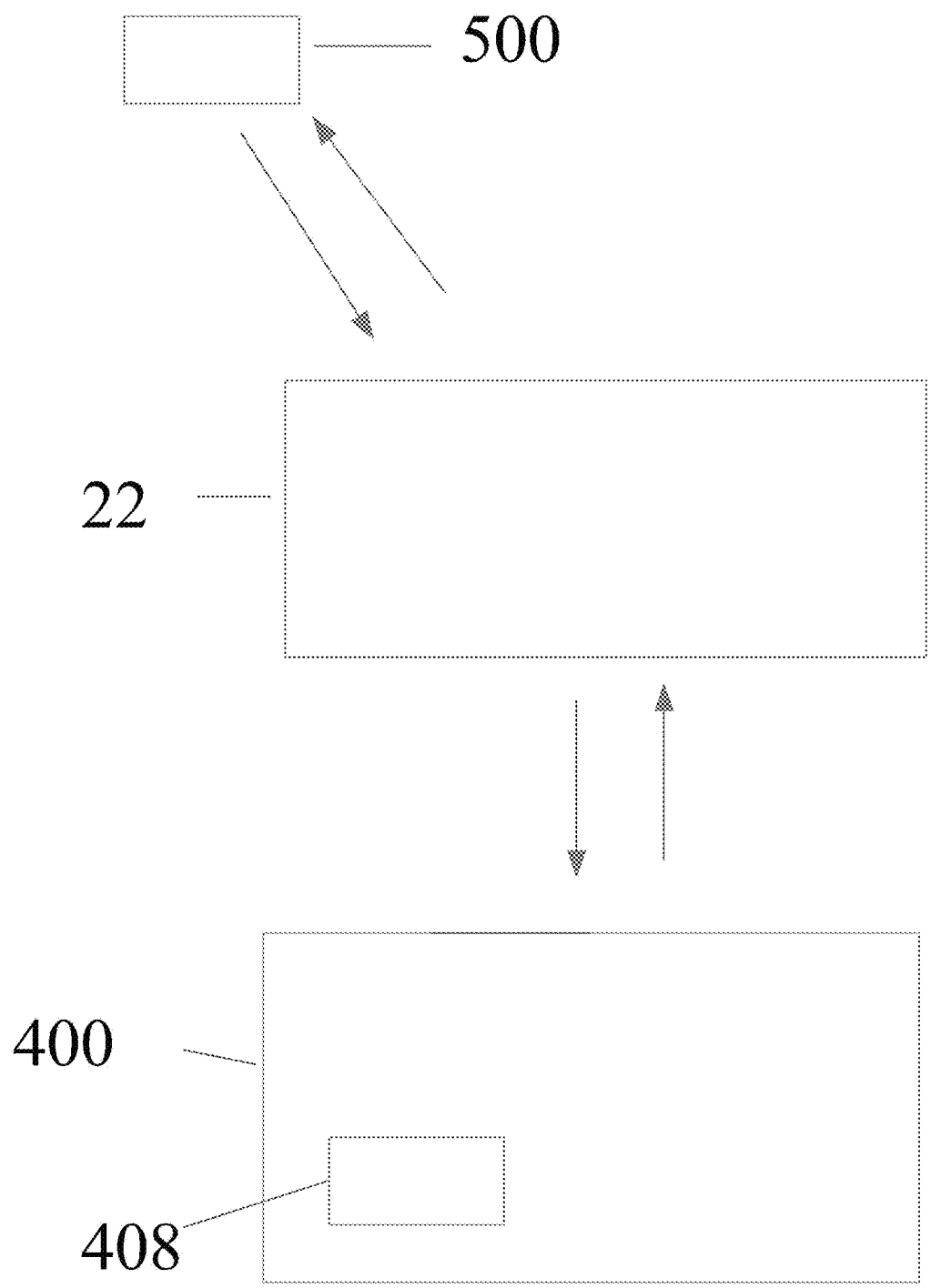
FIG. 14 illustrates the interrelationship of the portable data collection device and location determination device with the central database for providing location information.

As shown in FIG. 14, furthermore, it is preferred that when the occurrence of a drop off or pickup event is realized, the acknowledgment record of time and location as noted by the location determination device 408 is transferred to the central host 22 for updating the trip record of the individual member. In this manner, the location of a particular member may be accessed by an inquiry via the web portal 500 if desired.

For instance, as many members are elderly, it is desirable to ensure that that proper care in transporting the members to and from the respective facilities. By maintaining a centralized transport record which is accessible by an entity such as the broker, the respective location of a member may be accessed if desired.

In operation, if a family member would call in and ask if the whereabouts of a particular member, the member's location could be determined. Preferably, the trip record and affiliated status records are maintained at a central host facility 22 which is accessible via a web portal 500. By utilizing the unique trip identifier for a particular member, the respective trip and status of the trip could be retrieved via a web portal. The respective trip record would include the initial trip itinerary and the inclusion of the pickup acknowledgment and drop off acknowledgment records.

In addition to these records, it is preferred that the portable data collection device be accessible remotely and in particular that the location determination device may be utilized for identifying the respective location of the portable data collection device. In operation, the location determination device may periodically provide a data location record such as a geocode with respect to the location of the portable data location device and transmit this data location record back to the host site. Initially when the trip record is initiated by the driver during the initial creation of the transaction record, a tracking identifier is associated with the trip record. The tracking identifier could be an identifier unique to the driver, the vehicle or the portable data collection device. The geocode information for the respective portable data collection device is affiliated with the tracking identifier such that the trip record is periodically updated to identify the location of the vehicle via the portable data collection device.

Accordingly, when the location of a respective member is required, the individual member's trip record may be accessed. From the trip record it may be identified if the individual has been picked up, dropped off, or in transit and the general location of the vehicle may be determined. Also, for instance, the member, who is scheduled to be picked up at a specific time, may inquire with the central host, either via a phone, or via a web access portal utilizing their specific and unique trip identifier on the location of the vehicle. This would enable the member to identify the proximity of their respective ride. Such an inquiry may be done via an individual voice recognition system wherein the member may be provided with a tracking phone number and with the verbal input of the trip identifier, the latest location of the portable data collection device could be provided.

The location of the portable data location device in a real time scenario may provide information to both the member and the facility if delays are occurring. If the location of the device is immediately needed, the respective location determination device could be accessed remotely via a cellular or wireless communication system. The specific location determination device would be identifiable when the driver established the initial transaction record. When the initial transaction record was established it preferably noted the serial number of the portable data collection device which enables the location determination device to be accessible. Of course other means may be utilized for rendering the location determination device accessible such as assigning the portable data collection device with a unique transponder for being accessible and the identification of the portable data collection device being associated with the trip record when initiated by the driver. Accordingly, a location request signal may be sent out from the central host to the portable collection device wherein the location determination device will respond with a location geocode signal back to the host facility and update the corresponding trip record. This system will provide real time location information.

In addition to the aforementioned drop off and pickup acknowledgment records and affiliated geocode locations, similar acknowledgement records and affiliated geocode locations are created when the respective member is also picked up from the facility for a return trip home or to another facility appointment and also when dropped off. Each of the respective drop offs and pickups will have been previously identified in the manifest having the respective trip itineraries. Preferably each respective action of a drop off or a pickup has a corresponding notation with the trip itinerary.

To further insure the integrity of the system, the drop off facility may also include a web portal access device which may interact with the trip record for that respective member by updating the trip record of the member when the member actually arrives at the facility. The facility may require the member to sign in, or present some other unique member identifier. The trip record for the member would be updated to reflect the time and location of the member.

Figure 13:
FIG. 13 illustrates a driver sign off entry screen displayed by the portable data collection device according to the preferred embodiment of the present invention.

As shown in FIG. 13, once the driver has completed each trip on his manifest, the driver completes the trip transaction record upon return to the transportation provider facility or other predetermined end point. The driver's log would preferably reflect the completed manifest and the mileage for the day based upon an initial mileage inputted record and a final mileage inputted record. The driver utilizing the portable data collection device would complete the daily log and acknowledge the completed trips by finalizing a submission form and submitting the completed trip itineraries and manifest to the central host facility utilizing the wireless connectivity properties of the portable data collection device.

Upon submission of the transaction record, the validation of the rendering of the trips is undertaken. The respective geocodes of each pickup and drop off location are compared with the geocodes associated with the "scheduled" pickup and drop off locations. If discrepancies exist, the transportation provider may not receive reimbursement for the particular trip. Also, if discrepancies exist on the member identification utilized at the time of the pickups and drop offs, the transportation provider may not receive reimbursement for the particular trip.

In operation it may be seen that a more advantageous system for providing non-emergency medical transportation may be accomplished utilizing the presently described invention. First, a paperless system is established between the central broker system and the transportation provider for the identification of specific trips to be provided including the respective pickup and drop off locations and time. The paperless system includes a portable data collection device which may download trip itineraries designated for a particular driver or vehicle. Once the trip itineraries or manifest is downloaded, the driver may provide the requested transportation. During the course of the provision of these services the driver interacts with the portable data collection device identifying when members are picked up and dropped off. The portable data collection device notes the location and time of such activities. When the driver has completed the tasks for the specified duration, such as a day, the driver submits his completed tasks log by activating the transmission of the data from the portable data collection device to the central host computer via a wireless connection. The paperless system enables the real time submission of the completed log to the transportation broker which facilitates in a more rapid turnaround or payment process and also reduces data entry errors which translates into delayed processing times.

In addition to a paperless system, a system is established which checks the performance of the transportation provider. By utilizing geocodes associated with the initially established trip itinerary including the respective pickup and drop off locations, the performance and integrity of the provision of services may be monitored. The utilization of a portable data collection device having the ability to determine its respective location at any given time enables the independent provision of the actual location information of the respective pickups and drop offs to verify the provision of services when compared to the actual trip list.

Finally, by associating a respective trip identification with a particular member and associated portable data collection device which has a tracking system associated with it, the whereabouts of a particular member may be identified if desired. For instance, the portable data collection device provides an update of its location during a predetermined time interval. This location is updated to the central host which modifies the trip record to identify the location of the associated portable data collection device. This record may be retrieved via an individual voice recognition system, via a web portal, or other means. Furthermore, the respective portable data collection device may be sent a location signal which signals the portable location device to transmit its current location. Accordingly, in this manner, the real time location of an individual or vehicle may be assessed.

We claim:

1. A system for rendering patient transportation services via a third-party transportation provider from a residence to a medical facility and back, comprising:

a portable data collection device having an integrated location determination system, the portable data collection device also including a processor, an input device, and a wireless communication system;

the portable data collection device configured to display a trip schedule for the patient including a residence pickup location and residence pickup scheduled date and time and a medical facility drop off location and medical facility drop off scheduled date and time, the residence pickup location and the medical facility drop off location each associated with a respective location identifier, the trip schedule associated with a trip record stored at a central host remote from the portable data collection device and periodically updated via the wireless communication system;

the input device configured to receive input indicating occurrence of a pickup at the residence and output a residence pickup signal, the input indicating occurrence of the pickup includes receiving a unique member identifier of the patient, the unique member identifier corresponding to one or more of a signature of the patient, a social security number of the patient, a unique trip ID number assigned when the trip schedule was scheduled, a voice recording, a finger print rendering, or some other unique identifier of the patient;

the processor configured to, in response to receiving the residence pickup signal, automatically (a) record a location of the portable data collection device at the occurrence of the pickup at the residence as obtained from the location determination system and a date and time at the occurrence of the pickup at the residence, (b) update the trip record via the wireless communication system, and (c) establish a pickup location geocode for the pickup;

the input device configured to receive input indicating occurrence of a drop off at the medical facility and output a medical facility drop off signal;

the processor configured to, in response to receiving the medical facility drop off signal, automatically (a) record a location of the portable data collection device at the occurrence of the drop off at the medical facility as obtained from the location determination system and a date and time at the occurrence of the drop off at the medical facility, and (b) update the trip record via the wireless communication system;

the processor configured to periodically update the trip record by providing, via the wireless communication system, location information of the portable data collection device while the patient is in transit and before and after the residence pickup and before the medical facility drop off;

wherein the location identifier associated with the residence pickup location is compared to the location of the portable data collection device at the occurrence of the pickup at the residence as obtained from the location determination system and the residence pickup scheduled date and time is compared to the date and time at the occurrence of the pickup at the residence to produce a residence pickup validation;

wherein the location identifier associated with the medical facility drop off location is compared to the location of the portable data collection device at the occurrence of the drop off at the medical facility as obtained from the location determination system and the medical facility drop off scheduled date and time is compared to the date and time at the occurrence of the drop off at the medical facility to produce a medical facility drop off validation;

the portable data collection device configured to display the trip schedule for the individual including a medical facility pickup location and medical facility pickup scheduled date and time and a residence drop off location and residence drop off scheduled date and time, the medical facility pickup location and the residence drop off location each associated with a respective location identifier;

the input device configured to receive input indicating occurrence of a pickup at the medical facility and output a medical facility pickup signal;

the processor configured to, in response to receiving the medical facility pickup signal, automatically (a) record a location of the portable data collection device at the occurrence of the pickup at the medical facility as obtained from the location determination system and a date and time at the occurrence of the pickup at the medical facility, and (b) update the trip record via the wireless communication system;

the input device configured to receive input indicating occurrence of a drop off at the residence and output a residence drop off signal;

the processor configured to, in response to receiving the residence drop off signal, automatically (a) record a location of the portable data collection device at the occurrence of the drop off at the residence as obtained from the location determination system and a date and time at the occurrence of the drop off at the residence, and (b) update the trip record via the wireless communication system;

the processor configured to periodically update the trip record by providing, via the wireless communication system, location information of the portable data collection device while the patient is in transit and before and after the medical facility pickup and before the residence drop off;

wherein the location identifier associated with the medical facility pickup location is compared to the location of the portable data collection device at the occurrence of the pickup at the medical facility as obtained from the location determination system and the medical facility pickup scheduled date and time is compared to the date and time at the occurrence of the pickup at the medical facility to produce a medical facility pickup validation;

wherein the location identifier associated with the residence drop off location is compared to the location of the portable data collection device at the occurrence of the drop off at the residence as obtained from the location determination system and the residence drop off scheduled date and time is compared to the date and time at the occurrence of the drop off at the residence to produce a residence drop off validation; and wherein the reimbursement to the third-party transportation provider is denied where discrepancies exist in one or more of the residence pickup validation, the medical facility drop off validation, the medical facility pickup validation, and the residence drop off validation.

2. The system of claim 1, the wireless communication system configured to transmit results of the comparisons.

3. A system for rendering patient transportation services via a third-party transportation provider from a residence to a medical facility, comprising:

a portable data collection device having an integrated location determination system, the portable data collection device also including a processor, an input device, and a wireless communication system;

the portable data collection device configured to display a trip schedule for an individual or item including a residence pickup location and a medical facility drop off location, the residence pickup location and the medical facility drop off location each associated with a respective location identifier, the trip schedule associated with a trip record stored at a central host remote from the portable data collection device and periodically updated via the wireless communication system;

the input device configured to receive input indicating occurrence of a residence pickup and output a residence pickup signal, the input indicating occurrence of the residence pickup includes receiving a unique member identifier of the patient, the unique member identifier corresponding to one or more of a signature of the patient, a social security number of the patient, a unique trip ID number assigned when the trip schedule was scheduled, a voice recording, a finger print rendering, or some other unique identifier of the patient;

the processor configured to, in response to receiving the residence pickup signal, automatically (a) record a location of the portable data collection device at the occurrence of the residence pickup as obtained from the location determination system, (b) update the trip record via the wireless communication system, and (c) establish a pickup location geocode for the residence pickup;

the input device configured to receive input indicating occurrence of a medical facility drop off and output a medical facility drop off signal;

the processor configured to, in response to receiving the medical facility drop off signal, automatically (a) record a location of the portable data collection device at the occurrence of the medical facility drop off as obtained from the location determination system, and (b) update the trip record via the wireless communication system;

the processor configured to periodically update the trip record by providing, via the wireless communication system, location information of the portable data collection device while the patient is in transit and before and after the residence pickup and before the medical facility drop off;

the wireless communication system configured to transmit at least the locations of the portable data collection device at the occurrences of the residence pickup and the medical facility drop off as obtained from the location determination system for the locations to be compared to the location identifiers associated with the residence pickup location and the medical facility drop off location to produce a residence pickup validation and a medical facility drop off validation, respectively, and for denying reimbursement to the third-party transportation provider where discrepancies exist in one or more of the residence pickup validation and the medical facility drop off validation.

4. A system for rendering patient transportation services via a third-party transportation provider from a medical facility to a residence, comprising:

a portable data collection device having an integrated location determination system, the portable data collection device also including a processor, an input device, and a wireless communication system;

the portable data collection device configured to display a trip schedule for an individual or item including a medical facility pickup location and a residence drop off location, the medical facility pickup location and the residence drop off location each associated with a respective location identifier;

the input device configured to receive input indicating occurrence of a medical facility pickup and output a medical facility pickup signal, the input indicating occurrence of the medical facility pickup includes receiving a unique member identifier of the patient, the unique member identifier corresponding to one or more of a signature of the patient, a social security number of the patient, a unique trip ID number assigned when the trip schedule was scheduled, a voice recording, a finger print rendering, or some other unique identifier of the patient;

the processor configured to, in response to receiving the medical facility pickup signal, automatically (a) record a location of the portable data collection device at the occurrence of the medical facility pickup as obtained from the location determination system, (b) update the trip record via the wireless communication system, and (c) establish a pickup location geocode for the medical facility pickup;

the input device configured to receive input indicating occurrence of a residence drop off and output a residence drop off signal;

the processor configured to, in response to receiving the residence drop off signal, automatically (a) record a location of the portable data collection device at the occurrence of the residence drop off as obtained from the location determination system, and (b) update the trip record via the wireless communication system;

the processor configured to periodically update the trip record by providing, via the wireless communication system, location information of the portable data collection device while the patient is in transit and before and after the medical facility pickup and before the residence drop off;

the wireless communication system configured to transmit at least the locations of the portable data collection device at the occurrences of the medical facility pickup and the residence drop off as obtained from the location determination system for the locations to be compared to the location identifiers associated with the medical facility pickup location and the residence drop off location to produce a medical facility pickup validation and a residence drop off validation, respectively, and for denying reimbursement to the third-party transportation provider where discrepancies exist in one or more of the medical facility pickup validation and the residence drop off validation.

* * * * *